US00PP09932P

United States Patent [19]

Bridges

[11] Patent Number: Plant 9,932

[45] Date of Patent: Jun. 24, 1997

[54] MINIATURE ROSE PLANT NAMED 'BRIINCOG'

[76] Inventor: Dennis Alston Bridges, 2734 Toney Rd., Lawndale, N.C. 28090

[21] Appl. No.: 600,225

[22] Filed: Feb. 12, 1996

[51] Int. Cl.[6] ..... A01H 5/00

[52] U.S. Cl. ..... Plt./7.1

[58] Field of Search ..... Plt./7.1, 22

*Primary Examiner*—Howard J. Locker

[57] ABSTRACT

A new and distinct variety of miniature rose plant characterized by a profusion of exhibition form blooms that are an unusual combination of colors, consisting of mauve and yellow with a light fragrance, held on relatively long, strong stems.

1 Drawing Sheet

FIELD OF THE INVENTION

The present invention relates to a new and distinct variety of miniature rose plant which has been given the international variety recognition designation, 'Briincog', and is to be marketed in this country under the synonym 'Incognito'.

PLANTS RELATED TO THE INVENTION

The plant of this invention was originated as a result of a planned breeding program and controlled crossing which had as the seed parent the cultivar, 'Jean Kenneally' (U.S. Plant Pat. No. 5,637) and as the pollen parent, 'Twilight Trail' (U.S. Plant Pat. No. 6,198). The plant of the invention was a selection from the progeny of the stated cross, and has been asexually reproduced by the taking and rooting of stem cuttings. Such asexual reproduction as performed at Lawndale, N.C., has shown conclusively that the characteristic and distinctive features of the plant come true to form and are faithfully transmitted through succeeding propagations, thus establishing that 'Briincog' is stable.

'Briincog' is readily distinguished from its parents by the unusual color combination of lavender with yellow on the reverse of the petals, its stronger growth habit, and by its petal substance.

SUMMARY OF THE INVENTION

Among the new and novel characteristics which are possessed by this plant, which distinguish it from its parents and from all other miniature rose cultivars of which I am aware are:

1. Blooms of unusual mauve and yellow blend coloration that are well formed , blemish resistant, and show exceptional form and substance;

2. Abundant blooms which are borne singly, and in clusters of up to 7 blooms, on strong stems of from 4 to 7 inches in length;

3. A light fragrance;

4. An abundance of glossy, medium to dark green foliage which pleasingly contrasts with and highlights the blooms; and 5. Higher than usual disease resistance to common rose diseases with a higher than usual level of vigor, and growing to a height which is typical of roses of this market class to produce a plant which attractively appoints the home garden while providing cut flowers of exhibition form and quality.

BRIEF DESCRIPTION OF THE DRAWING

The single sheet of the accompanying drawing is a photographic illustration which shows foliage and typical specimens of the flowers of the new variety in different stages of development. Colors illustrated are as accurate and true as is reasonably possible to attain in color illustrations of this type. In this regard, it should be noted that the apparent yellow coloration in the upper surface of the petals is not a characteristic feature of the plant and may be due to reflectance. The petal coloration designations of the petal undersurface changes from the time the bloom begins to open, depending upon the temperature and weather conditions (for example, the warmer the weather, the deeper the yellow hues).

DETAILED BOTANICAL DESCRIPTION OF THE PLANT

The following is a detailed botanical description of my new variety of miniature rose, with color terminology in accordance with *The Royal Horticultural Society Colour Chart* (R.H.S.C.C.), except where common dictionary terms of color definition are employed.

Type: Hardy dwarf, bushy, compact, seedling greenhouse, outdoors, cut flower, garden decoration, potted plant.
Commercial class: Miniature.
International recognition name: 'Briincog'.
Commercial synonym: 'Incognito'.

The following observations were made from specimens grown outdoors at Cleveland County, N.C., USA, in June 1995.

The Flower

Blooming habit: Continuous.
Bud:
*Size.*—Medium.
*Length.*—1¼ cm just before opening.
*Form.*—Urn shaped.
*Color.*—When sepals first divide — Near 22D. When petals begin to unfurl — Inside: Near 185D. When half-brown — New 185D. Reverse side of petals: Near 162C edged with near 185D.
Sepals: As long as the bud (about 1¼ cm)—Several appendages appear on each sepal , same color as peduncle, near to 144A.
Peduncle: About 1 inch in length, Near to 145A, strong and erect.

Bloom:

*Size.*—About 1½ inches in diameter when fully expanded.

*Borne.*—Singly and in clusters of up to 7 blooms.

*Form.*—High-centered blooms reflex symmetrically, holding the high center.

*Form.*—High-centered blooms reflex symmetrically, holding the high center.

Petalage: About 23 to 25.

*Color.*—During the first two days: Inner petals at center of flower: Near to 185C. Outer petals: Near to 181C. Base of petals (point of attachment): Near to 12A. Reverse of petals: Near to 162C, tipped with near to 185D. General tonality from a distance: Mauve with shades of yellow on reverse of petals, near to 185D, with near to 162C.

*color change.*—As bloom ages it becomes slightly lighter, near to 186C. General tonality: Mauve with shades of yellow on reverse of petals, near 181D, with shades of near 162C on reverse of petals. After 3 or more days: Near to 186D, 186C, and 162D.

Petals:

*Texture.*—Thick, with good substance.

*Appearance.*—Velvety inside, satiny outside.

*Form.*—Urn-shaped, curling gently as bloom opens.

*Arrangement.*—Regular.

*Petaloids in center.*—Few.

*Persistence.*—Petals drop off cleanly.

*Fragrance.*—Light and fruity.

*Lasting quality.*—Flower lasts 3–5 days on the plant, and 2–3 days as a cut flower.

Reproductive Organs

Stamens, filaments and anthers:

*Arrangement.*—Regularly arranged around styles.

*Color.*—Yellow, near 14B.

*Pollen.*—Golden yellow, Near 15C.

Styles: Of uneven length, thin.

Stigmas: Near 11C in color.

Hips: About ¾ inches; globular in shape.

*Color.*—Medium green, near 191B, with light orange (near 31c) when mature.

*Seeds.*—Do not protrude.

The Plant

Form: Upright.

Growth: Vigrous, Uniform branching.

Height: About 18 to 25 inches when mature.

Foliage: Compound 3, 5, or 7 leaflets.

*Size.*—Medium for a miniature, each leaf is 3-4 cm in length.

*Quantity.*—Abundant.

*color.*—New foliage: Upper side is dark green, near 191A. Under side is lighter green, near 191B. Old foliage: Upper side is dark green, near 139B. Under side is lighter green, near 138B.

*Shape.*—Oval, pointed.

*Texture.*—Upper side is glossy. Under side has raised veins, small prickles on center vein.

*Edge.*—Serrated.

*Serration.*—Regular.

*Leaf stem.*—Upper side is near 182A in color. Under side is near 182B in color.

*Stipules.*—Medium length, slightly bearded.

*Disease resistance.*—Blackspot-good. Mildew-good. Rust-good.

Wood:

*New wood.*—Near 146A in color. Bark is smooth.

*Old wood.*—Near 146B in color. Bark is smooth.

Thorns: Ordinary quantity, base flat, medium length. Color when young is near 182B.

*Position.*—Irregular.

Prickles: None.

Winter hardiness: Winter hardy with little die back.

I claim:

1. A new and distinct variety of rose plant of the miniature rose class, substantially as herein shown and described, and characterized particularly as to novelty by its abundance of exhibition quality blooms of an unusual and striking combination of mauve and yellow, light fruity fragrance, firm thick petals, blooms being borne singly and in sprays of up to 7, a medium tall plant with dark green glossy foliage, said plant being easy to propagate from cuttings, and said blooms being relatively long lasting both on the plant and as cut flowers.

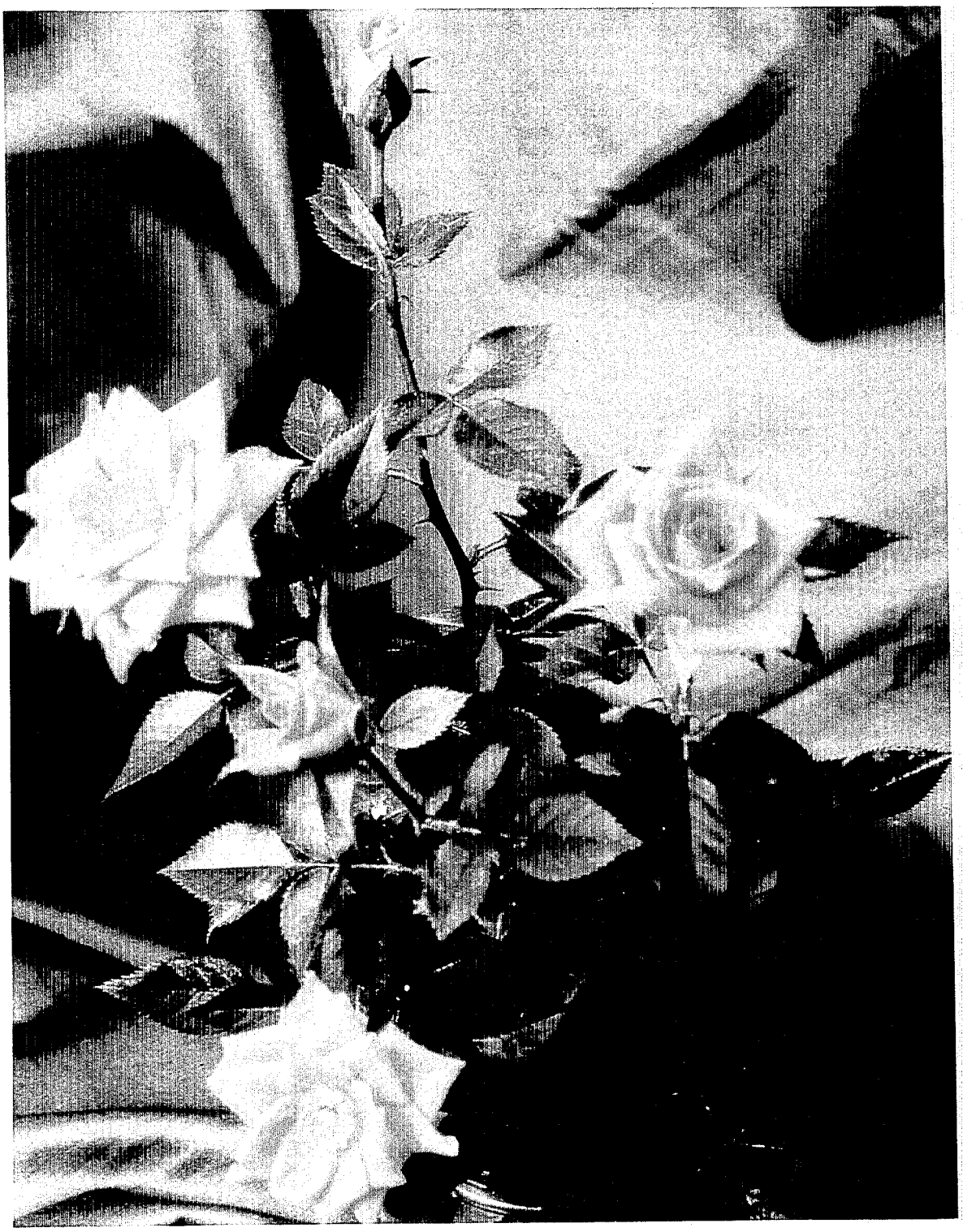

* * * * *